United States Patent [19]

Jansen

[11] Patent Number: 4,815,973

[45] Date of Patent: Mar. 28, 1989

[54] APPARATUS FOR CONNECTING DENTAL PROSTHESES AND DRILLING TEMPLATE FOR USE THEREWITH

[75] Inventor: Jozef Jansen, Rotterdam, Netherlands

[73] Assignee: Elgarden Aktiengessellschaft, Liechtenstein

[21] Appl. No.: 8,769

[22] Filed: Jan. 30, 1987

[30] Foreign Application Priority Data

Feb. 6, 1986 [CH] Switzerland ............................ 464/86

[51] Int. Cl.$^4$ ...................... A61C 13/12; A61C 13/225
[52] U.S. Cl. ...................................... 433/181; 433/141
[58] Field of Search ............... 433/181, 180, 182, 183, 433/191, 192, 193, 141, 176

[56] References Cited

U.S. PATENT DOCUMENTS

| 3,798,771 | 3/1974 | Edelman | 433/176 |
| 4,583,948 | 4/1986 | Jansen | 433/181 |

FOREIGN PATENT DOCUMENTS

| 0619856 | 10/1980 | Switzerland | 433/191 |
| 2117642 | 10/1983 | United Kingdom | 433/181 |
| 2117643 | 10/1983 | United Kingdom | 433/181 |
| 85/01872 | 5/1985 | World Int. Prop. O. | 433/181 |

*Primary Examiner*—John J. Wilson
*Attorney, Agent, or Firm*—Stevens, Davis, Miller & Mosher

[57] ABSTRACT

The apparatus comprises an anchoring element (2), a pin (3) fixed thereto, and a pin (4) rotatingly and pivotingly connected thereto. By means of a plastic handle (15) detachably affixed in a groove (13) of the anchoring element, this element can easily be inserted by its pins into matching boreholes (39, 47) in the tooth (38) serving as a support for the anchoring element. The telescoping drilling template (40) can be attached to the drill head (35) of a dental drill so that after the first hole (39) has been drilled in the tooth with a drill bit (36), the template is inserted in that hole, thus ensuring that the second hole (47) is drilled with the desired spacing corresponding to that of the two pins.

3 Claims, 3 Drawing Sheets

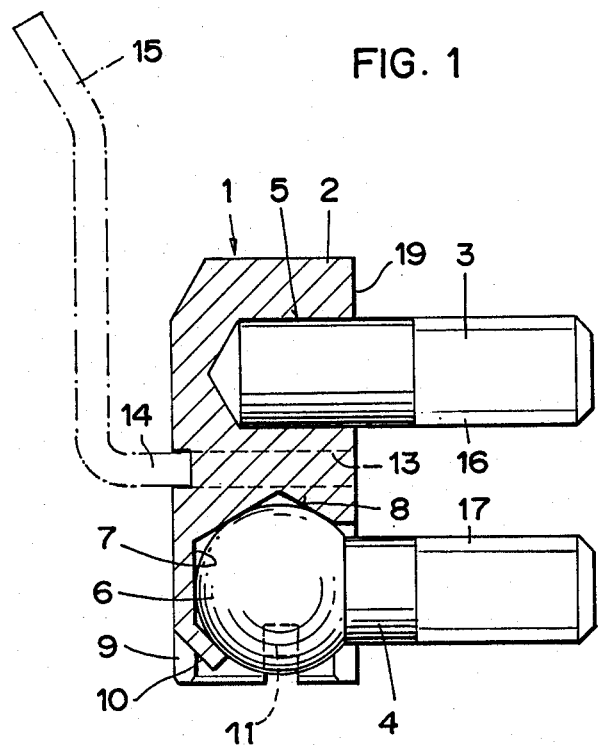
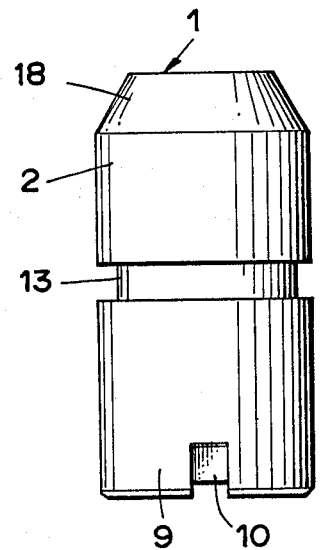
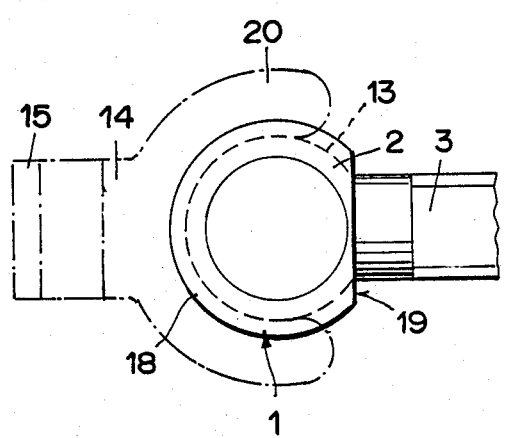
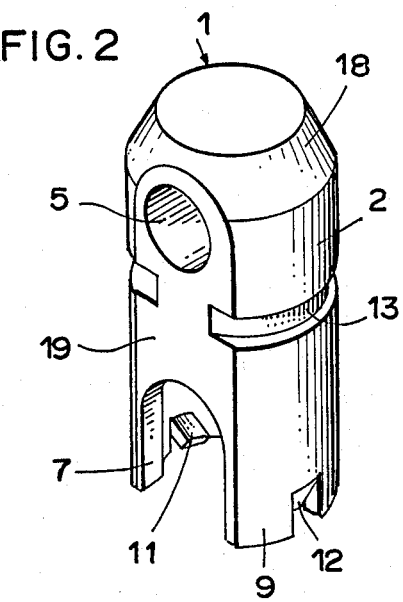

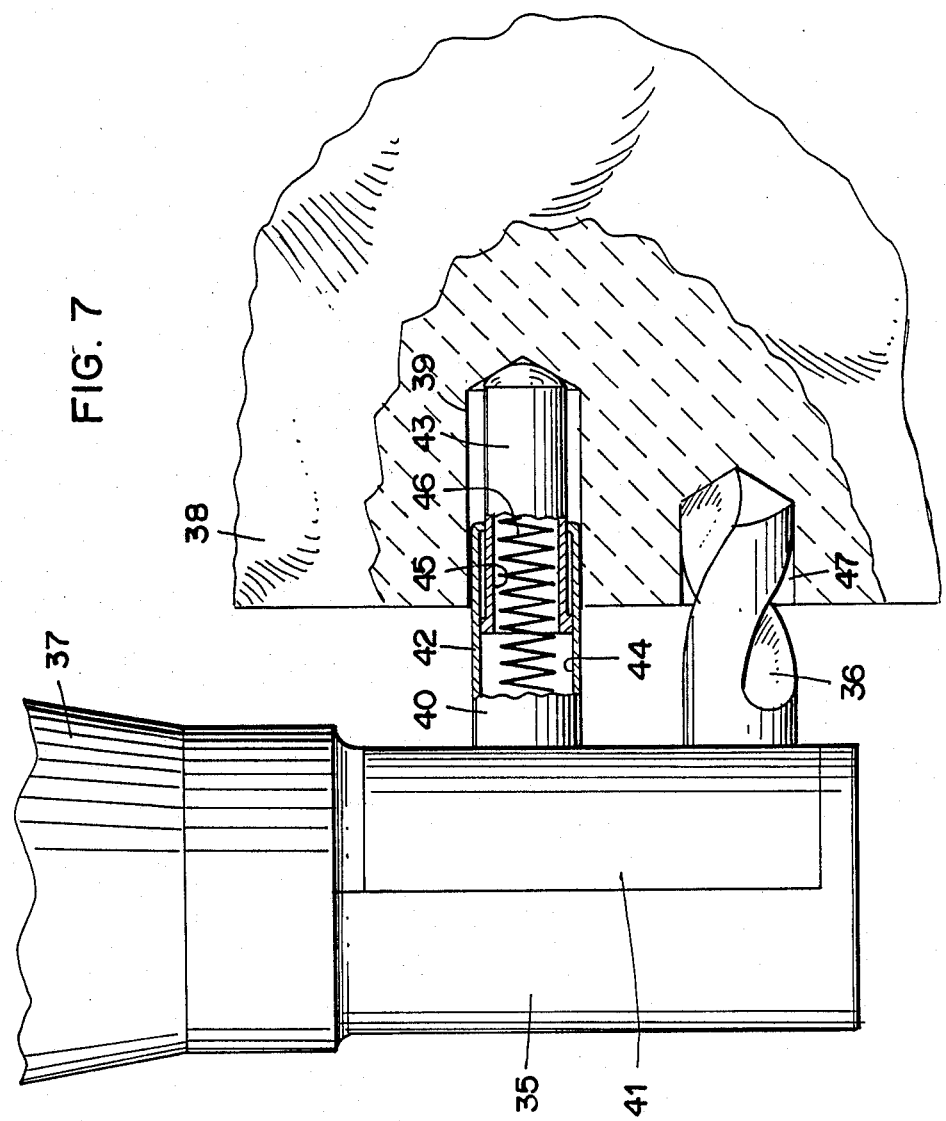

APPARATUS FOR CONNECTING DENTAL PROSTHESES AND DRILLING TEMPLATE FOR USE THEREWITH

This invention relates to dental prostheses, and more particularly to apparatus for connecting such prostheses, of the type having an anchoring element and two pins for engaging existing teeth or supports, as well as to a drilling template for drilling holes in an existing tooth or a support, these holes being intended to receive the pins of apparatus for connecting dental prostheses.

Apparatus for connecting dental prostheses, with pins to be cemented into an existing tooth, have been proposed. Such apparatus is connected to each tooth bounding a tooth gap. However, it is difficult for the dentist to drill two holes in the existing tooth in such a way that both the longitudinal axes of the holes and their spacing correspond exactly to the pins of the apparatus for connecting dental prostheses.

It is therefore an object of this invention to provide improved apparatus for connecting dental prostheses, as well as a drilling template for use with the drill head of a drill for dentistry purposes, by means of which the necessary holes for fixing the pins of the apparatus in the tooth can be drilled in a simple manner.

Until now, apparatus for connecting dental prostheses have been seized by the anchoring element with tweezers, so that very great skill on the part of the dentist has been required. It is therefore a further object of this invention to provide apparatus for connecting dental prostheses designed in such a way that in a convenient manner, it can be seized and inserted in the holes drilled in the tooth with the aid of the drilling template.

To this end, in the apparatus for connecting dental prostheses according to the present invention, one pin is rigidly joined to the anchoring element, and the other pin is mounted rotatably and/or pivotably in a recess in the anchoring element.

The drilling template according to the present invention has at least one pin to be introduced into a drilled hole.

Preferred embodiments of the invention and the manner of using them will now be described in detail with reference to the accompanying drawings, in which:

FIG. 1 is a longitudinal section through a first embodiment of the invention,

FIG. 2 is a perspective view of the embodiment of FIG. 1,

FIG. 3 is an elevation of the first embodiment,

FIG. 4 is a top plan view of the embodiment of FIG. 1,

FIG. 7 is an elevation of the front part of a drill head with a drilling template, shown partially in section, for drilling the holes in a tooth to receive the pins of the anchoring element.

Figure 5:
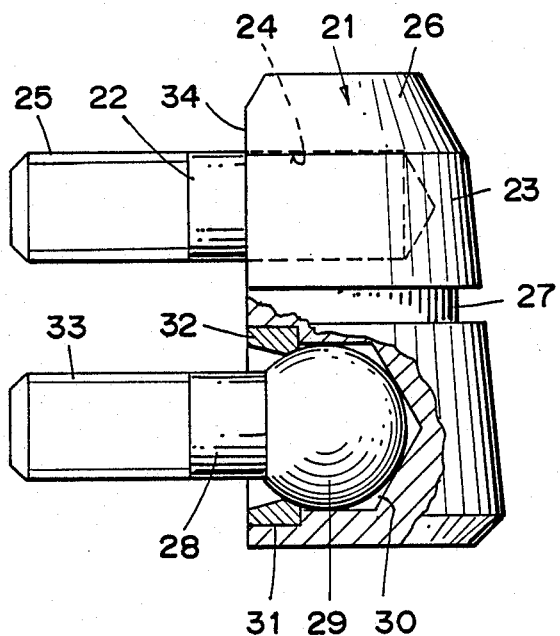
FIG. 5 is an elevation of a second embodiment, partially in section.

FIG. 1 is a longitudinal section through apparatus 1 for connecting dental prostheses in a first embodiment of the invention. Apparatus 1 comprises an anchoring element 2 and two pins 3 and 4 to be inserted in an existing tooth. Upper pin 3 is fixed rigidly in a recess 5 in anchoring element 2. Lower pin 4 is provided with a ball end 6 mounted rotatingly and pivotingly in a lower recess 7 of anchoring element 2. Lower recess 7 has a conical top 8. At the bottom of the cylindrical jacket 9 of anchoring element 2, retaining elements 10, 11, and 12 are cut into jacket 9 and bent in, and in the mid-region of anchoring element 2 there is a groove 13 for engaging the horizontal portion 14 of a plastic handle 15. By means of handle 15, pins 3 and 4 of anchoring element 2 can be more easily inserted in holes drilled in a tooth serving as a support for anchoring element 2. After anchoring element 2 has been thus inserted by its pins, handle 15 can be removed from groove 13. This manner of placing anchoring element 2 by means of handle 15 is simpler and more secure than seizing it with tweezers and introducing it. For mounting prostheses, an anchoring element 2 is inserted by means of pins 3 and 4 in each of the teeth bounding a tooth gap, and the prosthesis is then placed on the anchoring elements 2. Pins 3 and 4 further comprise regions 16 and 17 which may be provided with grooves so that the material used for cementing pins 3 and 4 in the boreholes in the tooth finds support between these grooves. On the side of anchoring element 2 adjacent to the tooth serving as a support, there is a flat surface 19.

FIG. 2 is a perspective view of the anchoring element of FIG. 1, this anchoring element being particularly suitable for use in the region of the incisors. The top 18 of anchoring element 2 is frustoconical. The spherical end 6 of lower pin 4 is held in recess 7 by bent-in retaining elements 10, 11, and 12 in the lower part of cylinder 9, pin 4 being introduced into the opening of recess 7 from below, and elements 10, 11, and 12 being bent in after insertion of ball end 6 into the opening.

FIG. 3 is a view of anchoring element 2 as seen from the direction of handle 15, while FIG. 4 is a top plan view of anchoring element 2 with handle 15. Lower end 20 of handle 15, engaging groove 13 of anchoring element 2, is forked and encircles the major part of the circumference of the anchoring element.

FIG. 5 is an elevation, partially in section, of an apparatus 21 for connecting dental prostheses in a second embodiment of the invention, particularly suitable for use in the region of the molars. An upper pin 22 is rigidly fixed in an opening 24 in an anchoring element 23. Pin 22 likewise has a grooved area 25 at the front. Element 23 is frustoconical at its top 26 and likewise includes a groove 27 for receiving the forked end of plastic handle 15. A lower pin 28 is rotatingly and pivotingly secured in anchoring element 23 by a spherical end 29 connected to pin 28. This pin is held in a recess 30 provided for ball end 29 in the lower part of anchoring element 23 by means of a ring 32 inserted in a circular recess 31 in the anchoring element. The front area 33 of lower pin 28 is preferably also provided with grooves. The side of anchoring element 23 facing the tooth serving as a support, into which pins 22 and 28 are inserted, is likewise a flat surface 34.

Figure 6:
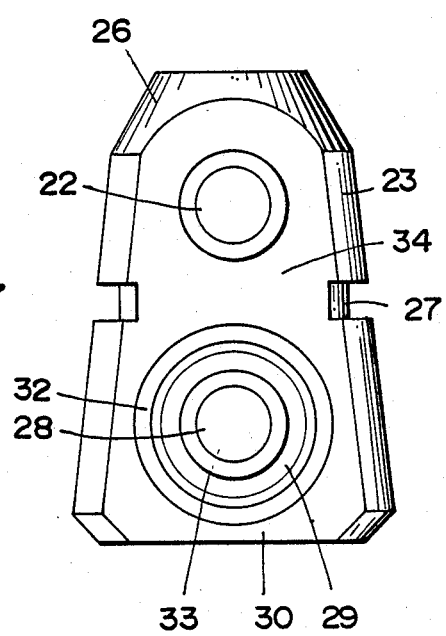
FIG. 6 is a front elevation of the embodiment of FIG. 5.

FIG. 6 is a front elevation of the apparatus according to the second embodiment as shown in FIG. 5, viewed from the side facing the tooth serving as a support. It will be seen that the outside surface of anchoring element 23 is conical except for flat face 34.

In FIG. 7, a drill head 35 with a drill bit 36 is shown. Drill head 35 adjoins the end 37 of the drill handle. First an upper borehole 39 is drilled with drill bit 36 in the tooth 38 serving as a support for the prosthesis. During this first drilling operation, no drilling template is as yet secured to drill head 35. Once upper hole 39 has been drilled, a drilling template 40 is mounted on drill head 35, e.g., by means of an attachment 41. Template 40 comprises two telescoped parts 42 and 43 having respective central recesses 44 and 45 in which a compression spring 46 is disposed. Template 40 is inserted in hole 39 already drilled in tooth 38, and a second, lower hole 47 is then drilled in the tooth with drill bit 36. During drilling of hole 47, the narrower front part 43 of template 40 telescopes into the wider part 42. This arrangement ensures that the two holes 39 and 47 are drilled parallel and with the desired constant spacing corresponding to the spacing between pins 3 and 4 or 22 and 28 of the apparatus for connecting dental prostheses. In the embodiment illustrated in FIG. 7, drilling template 40 and drill bit 36 are disposed one above the other in the longitudinal axis of drill head 35 and drill handle 37. However, template 40 and drill bit 36 might be disposed on a line perpendicular to the longitudinal axis of drill head 35 instead, depending upon whether holes 39 and 47 are to be drilled in an incisor or a molar.

What is claimed is:

1. An apparatus for connecting a dental prostheses having an anchoring element and two pins for engaging existing teeth or supports, one pin being rigidly joined to the anchoring element, and the other pin being mounted in a recess in the anchoring element in a manner which permits it to move in a rotating fashion, wherein the anchoring element has a groove disposed between the pins for detachably attaching a handle, wherein the anchoring element includes a handle inserted detachably laterally in said groove.

2. An apparatus for connecting a dental prostheses having an anchoring element and two pins for engaging existing teeth or supports, one pin being rigidly joined to the anchoring element, and the other pin being mounted in a recess in the anchoring element in a manner which permits it to move in a pivoting fashion, wherein the anchoring element has a groove disposed between the pins for detachably attaching a handle, wherein the anchoring element includes a handle inserted detachably laterally in said groove.

3. An apparatus for connecting a dental prostheses having an anchoring element and two pins for engaging existing teeth or supports, one pin being rigidly joined to the anchoring element, and the other pin being mounted in a recess in the anchoring element in a manner which permits it to move in a rotating and pivoting fashion, wherein the anchoring element has a groove disposed between the pins for detachably attaching a handle, wherein the anchoring element includes a handle inserted detachably laterally in said groove.

* * * * *